(12) United States Patent
Kang et al.

(10) Patent No.: US 12,099,647 B2
(45) Date of Patent: Sep. 24, 2024

(54) ELECTRONIC DEVICE FOR CONTROLLING A USER INTERFACE VIA A BIOMETRIC SENSOR AND CONTROL METHOD USING THE SAME

(71) Applicant: SAMSUNG ELECTRONICS CO., LTD., Suwon-si (KR)

(72) Inventors: Jae Min Kang, Suwon-si (KR); Seung Woo Noh, Suwon-si (KR); Byung Hoon Ko, Suwon-si (KR); Sang Yun Park, Suwon-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 18/129,413

(22) Filed: Mar. 31, 2023

(65) Prior Publication Data

US 2024/0192763 A1 Jun. 13, 2024

(30) Foreign Application Priority Data

Dec. 13, 2022 (KR) .......................... 10-2022-0173988

(51) Int. Cl.
*G06F 3/01* (2006.01)
*A61B 5/117* (2016.01)

(52) U.S. Cl.
CPC .............. *G06F 3/011* (2013.01); *A61B 5/117* (2013.01)

(58) Field of Classification Search
CPC ...... G06F 3/011; A61B 5/117; A61B 5/02116; A61B 5/0059; A61B 5/02225; A61B 5/742; A61B 5/7221; A61B 5/0053; A61B 5/1122; A61B 5/70; A61B 5/0002; A61B 5/02427; A61B 5/02438; A61B 2562/0233; A61B 2562/0247; A61B 2562/046; A61B 5/02007; A61B 5/0261; A61B 5/681; A61B 5/6843; A61B 5/6898; A61B 5/6826; A61B 5/02108; A61B 5/02416; A61B 5/743
See application file for complete search history.

(56) References Cited

U.S. PATENT DOCUMENTS 9,971,313 B2 5/2018 Chung
9,977,509 B2 5/2018 Park et al.
(Continued)

FOREIGN PATENT DOCUMENTS

JP 2020-135883 A 8/2020
KR 10-1520203 B1 5/2015
(Continued)

OTHER PUBLICATIONS

Extended Search Report issued Oct. 9, 2023 issued by the European Patent Office for EP Patent Application No. 23171679.6.

*Primary Examiner* — Rodney Amadiz
(74) *Attorney, Agent, or Firm* — Sughrue Mion, PLLC

(57) ABSTRACT

An electronic device and a control method using the same are provided. The electronic device may include: a photoplethysmography (PPG) sensor having a plurality of channels arranged isotropically; and a processor configured to: detect a center of gravity of an external force applied to a measurement area of the PPG sensor by an object, based on PPG signals that are detected from the plurality of channels when the object is in contact with the measurement area of the PPG sensor, and generate a control command based on a change in the detected center of gravity.

19 Claims, 29 Drawing Sheets

(56) References Cited

U.S. PATENT DOCUMENTS

| | | | |
|---|---|---|---|
| 10,216,278 | B2 | 2/2019 | Nakamura et al. |
| 10,867,448 | B2 | 12/2020 | Avrahami et al. |
| 11,241,197 | B2 | 2/2022 | Kang et al. |
| 11,287,888 | B2 | 3/2022 | Nakamura et al. |
| 2004/0169637 | A1* | 9/2004 | Sato .................... G06F 3/03547 |
| | | | 345/156 |
| 2007/0091063 | A1 | 4/2007 | Nakamura et al. |
| 2011/0050404 | A1 | 3/2011 | Nakamura et al. |
| 2013/0265148 | A1 | 10/2013 | Nakamura et al. |
| 2013/0265149 | A1 | 10/2013 | Nakamura et al. |
| 2013/0265254 | A1 | 10/2013 | Nakamura et al. |
| 2015/0253854 | A1 | 9/2015 | Nakamura et al. |
| 2015/0371510 | A1 | 12/2015 | Nakamura et al. |
| 2017/0031443 | A1 | 2/2017 | Nakamura et al. |
| 2019/0129506 | A1 | 5/2019 | Nakamura et al. |
| 2020/0019745 | A1 | 1/2020 | Kang et al. |
| 2020/0093377 | A1 | 3/2020 | Kwon et al. |
| 2022/0110535 | A1 | 4/2022 | Kang et al. |
| 2022/0175261 | A1* | 6/2022 | Li ....................... A61B 5/6826 |
| 2022/0233142 | A1 | 7/2022 | Hasan et al. |
| 2022/0409072 | A1 | 12/2022 | Kang et al. |

FOREIGN PATENT DOCUMENTS

| | | |
|---|---|---|
| KR | 10-2016-0025722 A | 3/2016 |
| KR | 10-2017-0059190 A | 5/2017 |
| KR | 10-2019-0043464 A | 4/2019 |
| KR | 10-2020-0002166 A | 1/2020 |
| KR | 10-2196962 B1 | 12/2020 |
| KR | 10-2022-0027610 A | 3/2022 |
| KR | 10-2022-0087104 A | 6/2022 |
| KR | 10-2022-0109240 A | 8/2022 |

* cited by examiner

ELECTRONIC DEVICE FOR CONTROLLING A USER INTERFACE VIA A BIOMETRIC SENSOR AND CONTROL METHOD USING THE SAME

CROSS-REFERENCE TO RELATED APPLICATION(S)

This application claims priority from Korean Patent Application No. 10-2022-0173988, filed on Dec. 13, 2023, in the Korean Intellectual Property Office, the disclosure of which is incorporated herein by reference in its entirety.

BACKGROUND

1. Field

Apparatuses and methods consistent with example embodiments relate to configuring a user interface (UI) controller using a biometric sensor, and controlling various devices using the UI controller.

2. Description of the Related Art

In today's word, various technologies are available for controlling the user interface (UI) of devices, including joysticks and touchscreens. However, incorporating a joystick into a mobile device can be challenging due to a physical size of components of the joystick. Similarly, using a touchscreen for UI control can be difficult due to the limited screen size. To overcome these challenges, motion recognition technology is available, which allows users to control device functions by recognizing movements of an entire body or a portion of the body of a user, such as a torso, a hand, a face and the like of the user. This technology can utilize different methods such as detecting a change in an electronic signal generated by muscles using an electromyogram (EMG) sensor and estimating a gesture performed by a user based on the detected change, and measuring an inertia from a physical movement of a user using a motion sensor such as an accelerometer and a gyroscope and estimating a gesture performed by the user based on the measured inertia.

SUMMARY

According to an aspect of the present disclosure, an electronic device may include: a photoplethysmography (PPG) sensor having a plurality of channels arranged isotropically: and a processor configured to: detect a center of gravity of an external force applied to a measurement area of the PPG sensor by an object, based on PPG signals that are detected from the plurality of channels when the object is in contact with the measurement area of the PPG sensor; and generate a control command based on a change in the detected center of gravity.

The PPG sensor may include at least one light source configured to emit light to the object, and at least one detector configured to detect light scattered or reflected from the object, wherein a combination of the at least one light source and the at least one detector may provide the plurality of channels.

The processor may be further configured to: obtain low-frequency band signal values of the PPG signals that are detected from the plurality of channels, in a predetermined low frequency band: and detect the center of gravity based on the low-frequency band signal values of the plurality of channels.

The processor may be further configured to: generate an intensity map by mapping the obtained low-frequency band signal values of the plurality channels to a circular circumference; and detect the center of gravity based on the intensity map.

The processor may be further configured to: obtain low-frequency band signal values for a plurality of virtual channels arranged on the circular circumference by performing interpolation on the low-frequency band signal values of the plurality of channels that are arranged on the circular circumference; and generate the intensity map based on the low-frequency band signal values of the respective channels and the low-frequency band signal values of the virtual channels to the circular circumference.

The electronic device may include a main body including the PPG sensor and the processor are disposed, wherein the processor may be further configured to detect a change in the center of gravity that is caused by at least one of a change in pressure applied to the PPG sensor or the main body, and movement of the main body or the object, while the PPG sensor is in contact with the object.

The electronic device may include a main body including the PPG sensor, the processor, and an input interface, wherein the processor may be further configured to generate the control command based on a change in the detected center of gravity.

The processor may be further configured to control the electronic device or a an external device connected to the electronic device, via the control command.

The processor may be further configured to generate the control command to control a function of estimating bio-information, based on the PPG signals of the plurality of channels.

The external device may include at least one of a game console, a robot, a drone, an automobile, a TV, a machine, a mobile device, and an Internet of Things (IOT) device.

The electronic device may include a communication interface configured to transmit the control command to the external device.

The electronic device may include a display, wherein in response to a user's request for control, the processor may be further configured to provide a user interface for controlling the display via the control command.

The processor may be further configured to control the user interface to display a graphic object responsive to the change in the center of gravity on the display, and change representation of the graphic object in synchronization with the change in the detected center of gravity.

The electronic device may include a communication interface configured to receive data from another electronic device, wherein the processor may be further configure to display a graphic object associated with the received data on the user interface.

According to another aspect of the present disclosure, a control method using an electronic device, may include: by a photoplethysmography (PPG) sensor having a plurality of channels arranged isotropically, measuring PPG signals from an object through the plurality of channels; detecting a center of gravity of an external force applied to a measurement area of the PPG sensor by the object, based on the PPG signals that are detected from the plurality of channels when the object is in contact with the measurement area of the PPG sensor: and generate a control command based on a change in the detected center of gravity.

The detecting of the center of gravity may include: obtaining low-frequency band signal values from the PPG signals that are detected from the plurality of channels, in a predetermined low frequency band: and detecting the center of gravity based on the low-frequency band signal values of the plurality of channels.

The detecting of the center of gravity may include: generating an intensity map by mapping the low-frequency band signal values of the plurality of channels to a circular circumference; and detecting the center of gravity based on the intensity map.

The control method may include, in response to a user's request for control, displaying a user interface for controlling a display of the electronic device according to the control command.

The displaying of the user interface may include: displaying a graphic object responsive to the change in the center of gravity on the user interface: and changing representation of the graphic object in synchronization with the change in the detected center of gravity.

According to another aspect of the present disclosure, an electronic device may include: a memory including one or more instructions: and one or more processors which, in response to a user's request, are configured to execute the one or more instructions to selectively perform a function control operation and a bio-information estimation operation, wherein the function control operation may include: receiving, from a photoplethysmography (PPG) sensor having a plurality of channels arranged isotropically, PPG signals: detecting a center of gravity of an external force applied to a measurement area of the PPG sensor by an object, based on the PPG signals that are detected from the plurality of channels when the object is in contact with the measurement area of the PPG sensor; and performing the function control operation based on the detected center of gravity.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
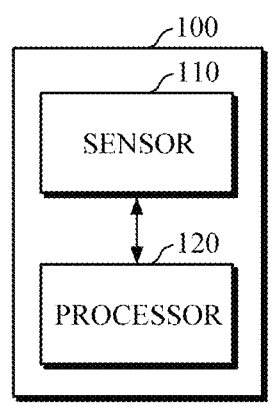
FIG. 1 is a block diagram illustrating an electronic device according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a block diagram illustrating an electronic device according to an embodiment of the present disclosure.

Examples of the electronic device may include a smartphone, a tablet PC, a desktop computer, a laptop computer, or a wearable device in the form of a smartwatch, a bracelet, a wristband, a ring, glasses, a headband, etc., but the electronic device is not limited thereto.

Referring to FIG. 1, an electronic device 100 includes a sensor 110 and a processor 120.

The sensor 110 may measure a bio-signal from an object, and may be also referred to as a biometric sensor. The object may be a body part where bio-signals may be easily measured and may be a wrist skin area that is adjacent to the radial artery, or a skin area where capillary blood or venous blood passes, or a peripheral part of the body with high blood vessel density, such as fingers, toes, and the like. The bio-signal may be Photoplethysmogram (PPG), Electrocardiogramactromyography (EMG), impedance plethysmogram (IPG), Pressure wave, video plethysmogram (VPG), etc., but is not limited thereto. The following description will be given using a PPG signal as an example.

The sensor 110 may include a light source for emitting light to an object and a detector for detecting light returning after scattering or reflection from or transmission into the skin surface of the object or body tissue such as blood vessels and the like. At least one of the light source and the detector may be provided in plurality. At least two or more of a plurality of light sources may emit light of different wavelengths, such as green, blue, red, and infrared wavelengths, and the like. The light source may include a light emitting diode (LED), a laser diode (LD), a phosphor, and the like. The detector may include a photo diode, a photo transistor (PTr), an image sensor (e.g., complementary metal-oxide semiconductor (CMOS) image sensor), and the like. The sensor 110 may include a plurality of channels arranged isotropically at a predetermined distance from the center of the sensor, and at least one of the light source and the detector may be disposed in each of the plurality of channels.

The processor 120 may be electrically or functionally connected to the sensor 110 to control the sensor 110. When a user requests a function control, the processor 120 may operate in a function control mode, and may recognize a user's intention, such as a gesture for moving, rotating, enlarging, reducing, or selecting. The processor 120 may control a function corresponding to the user's intention, which may be a function of the electronic device 100 or a function of another device connected to the electronic device 100. For example, the function may include a function of executing applications (e.g., music, settings, health (bio-information estimation), photo, social networking service (SNS) application, clock, memo, etc.) installed in the electronic device 100 or another electronic device, a function of controlling menus in the executed application, and/or a function of controlling movement of another device, and the like. Examples of other devices that can be controlled may include a game console, a robot, a drone, an automobile, TV, a machine (e.g., various machines in a smart factory including components), a mobile device, and an Internet of Things (IOT) device (e.g., refrigerator, microwave oven, washing machine, home network, lighting device, cooling and heating device, etc.), a smartphone, a tablet PC, a desktop computer, and the like.

The processor 120 may use isotropic multiple channels to continuously measure a plurality of PPG signals within a measurement area of the sensor 110 to detect the center of gravity. The processor 120 may then perform function control based on a change in the detected center of gravity. The processor 120 may generate a control signal (or a control command) corresponding to the detected change in center of gravity, and may transmit the generated control signal (or the generated control command) to another device through a communication interface. While touching the sensor 110 with an object, a user may input their intention by moving or rotating a main body of the electronic device 100 or the object in a predetermined direction, or by pressing the object against the main body or by pressing the sensor against the object, and the like. The processor 120 may track a change in the center of gravity (such as change in position and/or intensity of the center of gravity) based on a user's motion, and may perform function control based on the change in the center of gravity. As such, the processor 120 may detect the center of gravity within the sensor's measurement area using PPG signals, generate a control signal based on changes in the center of gravity, and perform a function control accordingly.

In response to the user's request for function control, the processor 120 may display a user interface for function control on a display. The user interface may include a graphic object responsive to the change in the center of gravity, a graphic object associated with function control, a graphic object representing a change trajectory, and/or a graphic object representing a user's gesture in response to the change in the center of gravity, and the like. In response to the detection of the center of gravity, the processor 120 may change representation (e.g., movement, shape, form, color, etc.) of a graphic object displayed on the user interface.

Figure 2:
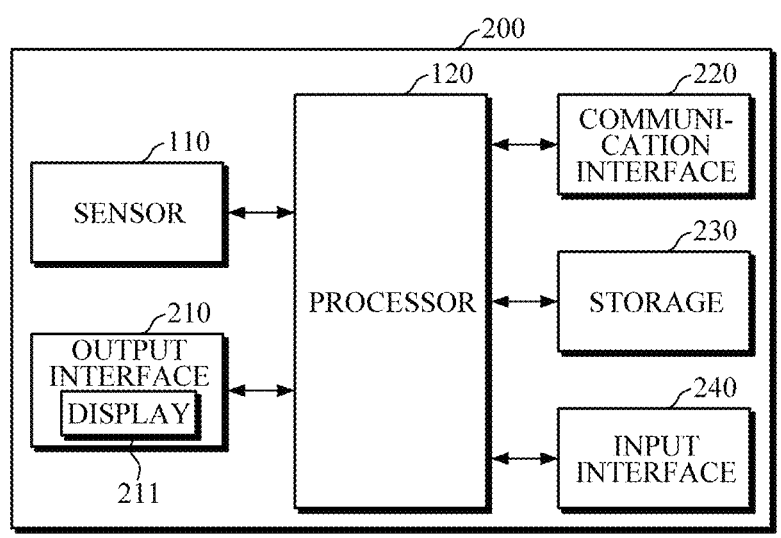
FIG. 2 is a block diagram illustrating an electronic device according to an embodiment of the present disclosure.

Referring to FIG. 2, an electronic device 200 may include the sensor 110, the processor 120, an output interface 210, a communication interface 220, a storage 230, and an input interface 240. Some of the sensor 110, the output interface 210, the communication interface 220, the storage 230, and the input interface 240 may be omitted if necessary or may be included in another device which is physically separated. The sensor 110 and the processor 120 are described above, such that a description thereof will be omitted.

The output interface 210 may include a display 211, and in response to the processor 120 processing data, the output interface 210 may output the processed data to the display 210. For example, when the processor 120 configures the user interface to serve a function to be controlled in response to a request for function control, the output interface 210 may output the configured user interface to the display 210. In addition, in response to the processor 120 detecting the center of gravity and generating information on a graphic object displayed in the user interface based on the change in the center of gravity, the output interface 210 may modify representation of a corresponding graphic object. However, the output interface 210 is not limited thereto and may output information, such as a bio-signal measured by the sensor 110, a function control result, and the like. The output interface 210 may further include an audio output module and/or a haptic module, etc., in addition to the display 211, and may output necessary information in a non-visual manner using sounds, vibrations, tactile sensation, and the like.

Under the control of the processor 120, the communication interface 220 may be connected to an external device by using wired and wireless communication techniques to transmit and receive various data. For example, in response to the processor 120 generating a control signal for function control of other device to be controlled, the communication interface 220 may transmit the generated control signal to the other device. In addition, the communication interface 220 may receive, from the other device, data generated as a result of the control and may transmit the generated data to the processor 120. The communication interface 220 may receive a PPG signal for function control from a sensor mounted in the external device. Alternatively, the communication interface 220 may transmit the PPG signal, measured by the sensor 110 of the electronic device 200, to the external device so that the external device may perform function control. In this case, the external device may be a device different from the device of which function is to be controlled.

The wired and wireless communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, 3G, 4G, and 5G communications, and the like. However, the communication techniques are not limited thereto.

The storage 230 may store programs (application software) to be executed by the processor 120. The programs may include one or more instructions for performing various functions of the electronic device 200, including the aforementioned function control operation. In addition, the storage 230 may store a variety of information associated with function control, which is to be referred to by the processor 120 and includes, for example, a pattern of change in the center of gravity of each device to be controlled, a control function (or a control command) matched with the pattern of change in the center of gravity, and the like. In addition, the storage 230 may store user interface configuration information related to function control which is to be referred to by the processor 120, and information related to modifying the representation of a graphic object. Further, the storage 230 may store information, such as the bio-signal measured by the sensor 110, user information (age, gender, height, weight, health information, etc.), bio-information estimation model, and the like.

The storage 230 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 3A:
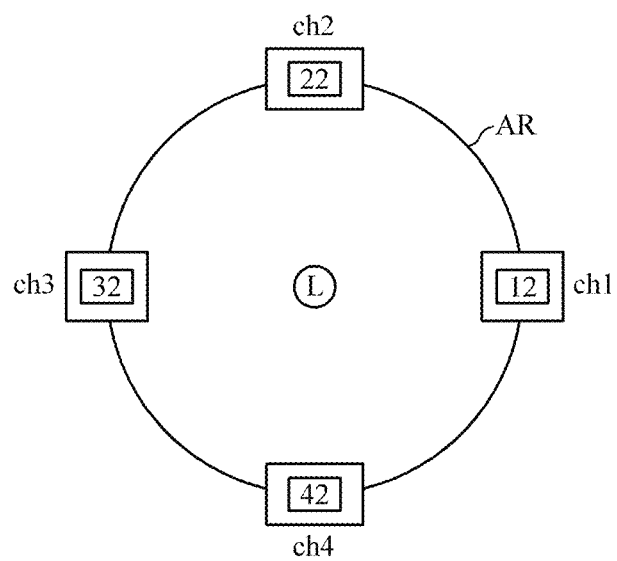
FIGS. 3A to 3C are diagrams explaining a structure of a PPG sensor.
Figure 3B:
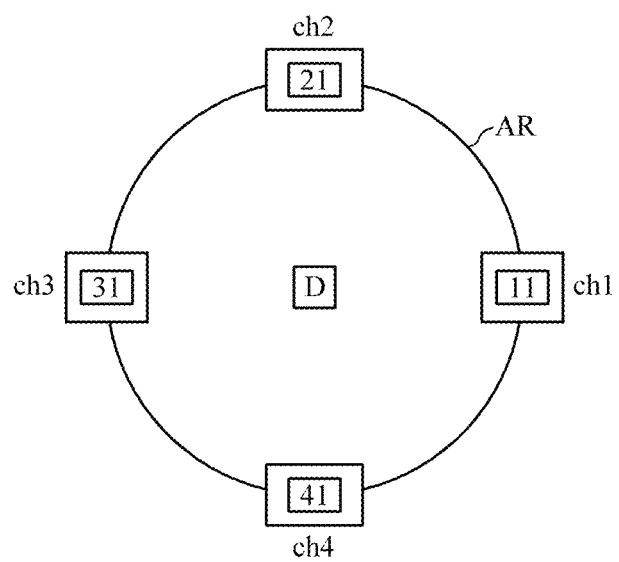
Figure 3C:
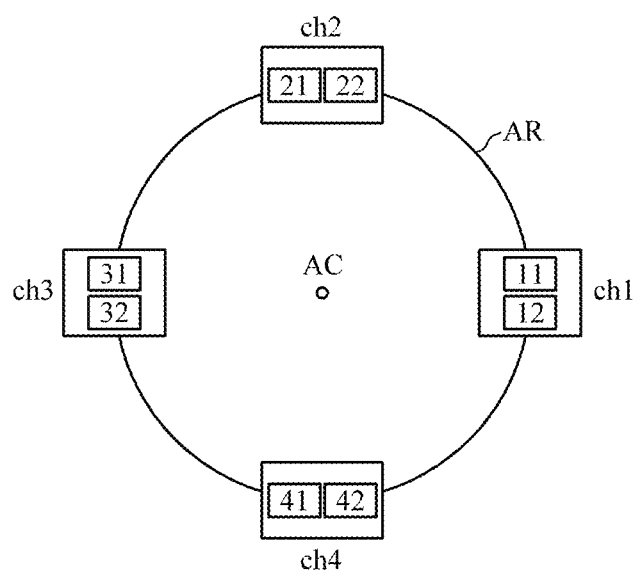

The input interface 230 may receive, from a user, instructions and/or data to be processed by the processor 120. The input interface 230 may include a control button (e.g., stem of a smartwatch, volume/power button of a smartphone, etc.) of the electronic device 200, a touch screen of the display, a microphone, a mouse, a keyboard, a digital pen (e.g., stylus pen, etc.). The processor 120 may perform function control based on a user command input through the input interface 230, along with the change in the center of gravity described above. FIGS. 3A to 3C are diagrams explaining a structure of a PPG sensor.

Referring to FIG. 3A, one or more light sources L are disposed at the center of the sensor 110, and a plurality of channels ch1, ch2, ch3, and ch4 may be arranged isotropically at a predetermined position relative to the center of the sensor. The channels may refer to individual light-sensitive components that detect changes in blood volume in the tissue being measured. The channels may be constituted with a light source (such as an LED) and a light detector (such as a photodiode) that work together to measure changes in light absorption caused by variations in blood volume in the tissue. PPG sensors may use multiple channels to measure changes in different parts or different areas of the body.

According to an embodiment of the present disclosure, the plurality of channels ch1, ch2, ch3, and ch4 are have an isotropic arrangement, and therefore a measurement area may be formed in a predetermined shape (e.g., circle). While four channels are illustrated herein, the number of channels is not limited thereto. Each of the plurality of channels ch1, ch2, ch3, and ch4 may include one or more detectors 12, 22, 32, and 42, and may detect light reacting with an object after light is emitted by the light sources L, disposed at the center, to the object when the object is in contact with the measurement area AR. The isotropic arrangement may have a circular array of the detectors 12, 22, 32, and 42, where each detector is positioned at an equal distance of the center of the circle. Specifically, the light sources L disposed at the center may be turned on in a time-division manner, and the channels ch1, ch2, ch3, and ch4 arranged isotropically may be driven sequentially or simultaneously to detect light. For example, the channels ch1, ch2, ch3, and ch4 may be driven sequentially in a clockwise direction, counterclockwise direction, diagonal direction, etc., or two or more of the channels may be driven simultaneously.

Referring to FIG. 3B, one or more detectors D may be disposed at the center of the sensor 110, and a plurality of channels ch1, ch2, ch3, and ch4 may be arranged isotropically at a predetermined position from the center of the sensor. Each of the plurality of channels ch1, ch2, ch3, and ch4 may include one or more light sources 11, 21, 31, and 41. When an object comes into contact with the measurement area AR, the light sources 11, 21, 31, and 41 of the respective channels ch1, ch2, ch3, and ch4 may be turned on in a time-division manner in a predetermined order (clockwise direction, counterclockwise direction, diagonal direction, etc.), and the detectors D disposed at the center may detect light reacting with the object.

Referring to FIG. 3C, the sensor 110 includes a plurality of channels ch1, ch2, ch3, and ch4 arranged isotropically at a predetermined position from a center AC, and the respective channels ch1, ch2, ch3, and ch4 may include one or more light sources 11, 21, 31, and 41, and detectors 12, 22, 32, and 42. The plurality of channels may be driven sequentially or simultaneously in a predetermined pattern (clockwise direction, counterclockwise direction, or diagonal direction). For example, when the light source 11 of channel 1 ch1 is driven, the detector 32 of channel 3 ch3, located diagonally opposite thereto, may be driven simultaneously.

FIGS. 4A to 4F are diagrams explaining an example of detecting a center of gravity based on contact of an object.

Figure 4A:
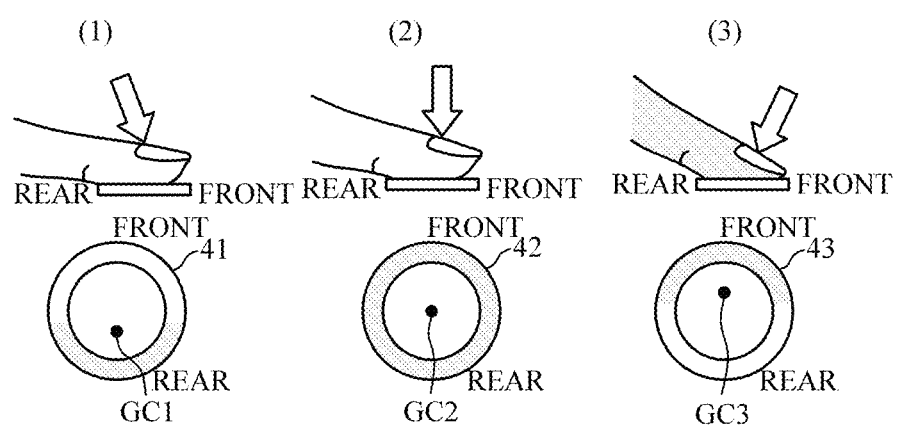
FIGS. 4A to 4F are diagrams explaining an example of detecting a center of gravity based on contact of an object.

FIG. 4A is a diagram illustrating a change in center of gravity and intensity map according to a change in pressing direction or position of a finger on the measurement area AR. Cases (1) and (3) of FIG. 4A illustrate that when feature points of the finger show a non-uniform pressing force in a vertical direction to the center of the measurement area AR, with the force applied to the lower side and the upper side, respectively, centers of gravity GC1 and GC3 are located at the lower side and the upper side of intensity maps 41 and 43. Case (2) pf FIG. 4A illustrates a uniform pressing force applied vertically to the center of the measurement area AR, resulting in a center of gravity GC2 located at the center of an intensity map 42. As described above, changing a contact direction or pressure applied to the measurement area AR of the sensor 110 may cause a shift in the center of gravity.

Figure 4B:
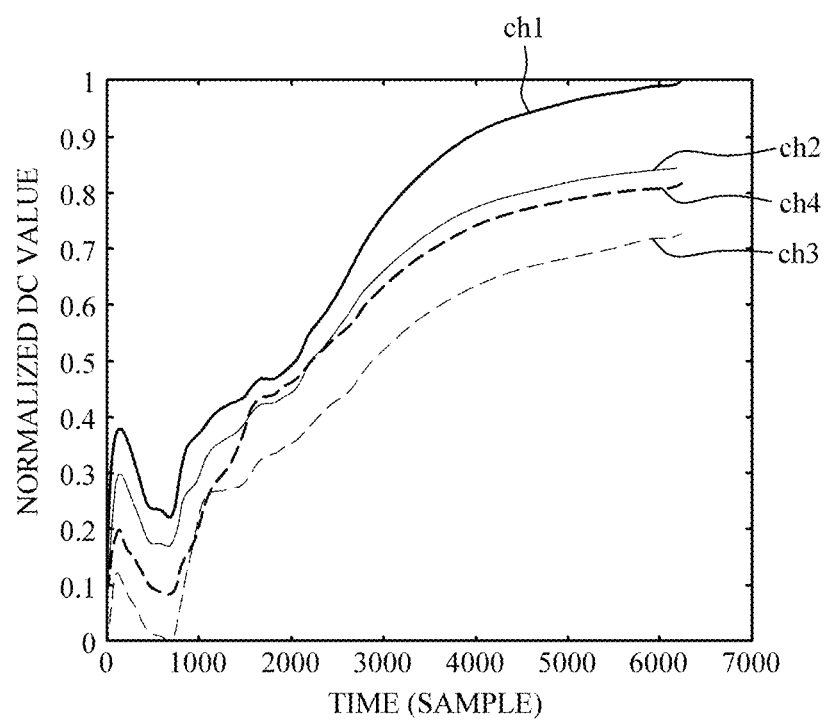

FIG. 4B is a diagram illustrating low-frequency band signals of PPG signals measured by the respective channels ch1, ch2, ch3, and ch4 of the sensor 110. When a user applies varying pressure to the sensor 110 with an object, the intensity of a low-frequency band signal component may change. The processor 120 may extract low-frequency band signals of the respective channels ch1, ch2, ch3, and ch4 by filtering the PPG signals of the respective channels ch1, ch2, ch3, and ch4. The low-frequency band signals may indicate signals in a frequency range of 0 Hz to 0.3 Hz among the measured PPG signals. In addition, the processor 120 may normalize the extracted low-frequency band signals of the respective channels ch1, ch2, ch3, and ch4. For example, the processor 120 may normalize the low-frequency band signals for each channel by dividing the low-frequency band signal value by a maximum value, thereby ensuring that the low-frequency band signals have a normalized range of 0 to 1 at each time.

Figure 4C:
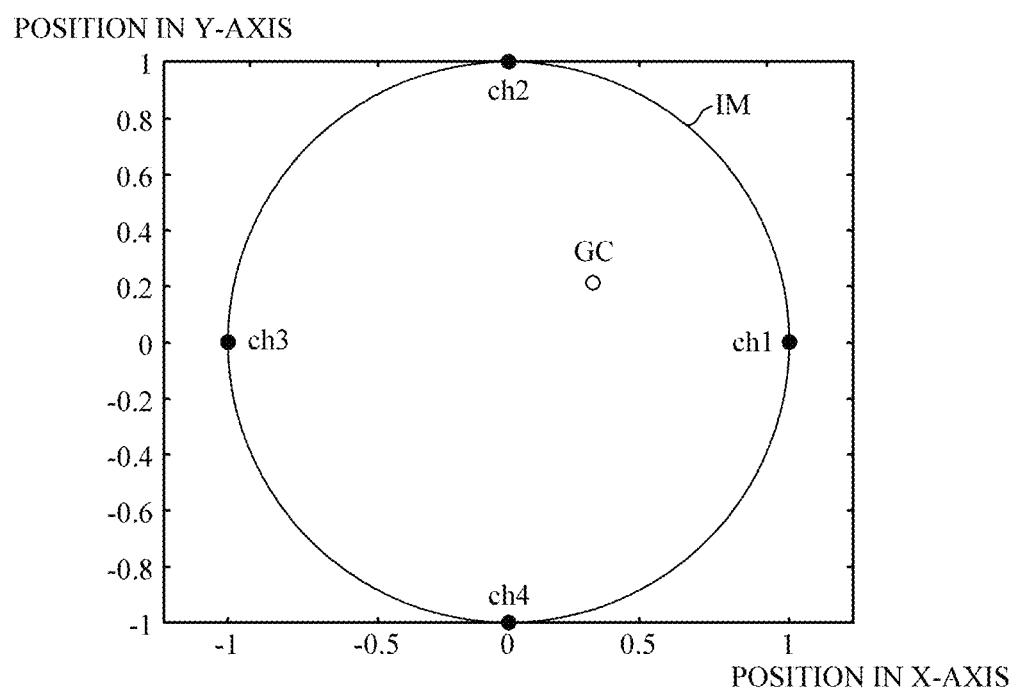
Figure 4D:
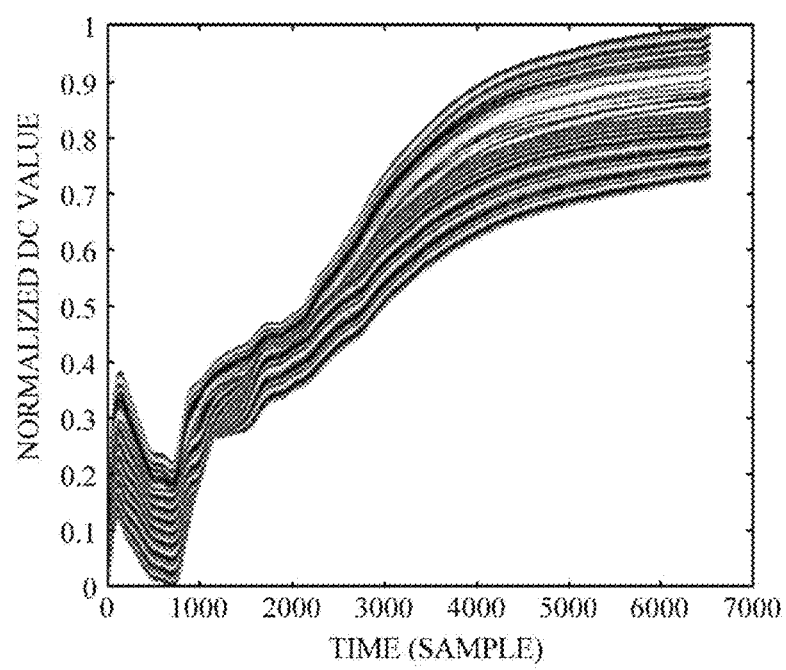

FIG. 4C is a diagram explaining an intensity map according to a change in center of gravity. The processor 120 may generate an intensity map IM at each time by mapping low-frequency band signal values (normalized values) at each time from the respective channels ch1, ch2, ch3, and ch4 to corresponding positions on a circular circumference having a radius of 1. The processor 120 may detect a center of gravity GC based on the generated intensity map IM at each time. By further providing a plurality of virtual channels on the circular circumference (where the actual channels ch1, ch2, ch3, and ch4 do not exist), and by performing circular interpolation on the obtained low-frequency band signal values of the actual channels ch1, ch2, ch3, and ch4, the processor 120 may obtain low-frequency band signal values for the plurality of virtual channels. FIG. 4D is a diagram illustrating low-frequency band signals of all channels (e.g., 120 channels) including low-frequency band signal components of virtual channels. The processor 120 may generate the intensity map IM at each time by mapping the low-frequency band signal values at each time of all the channels to corresponding positions on a circular circumference, and may detect the center of gravity at each time based on the generated intensity map IM.

Figure 4E:
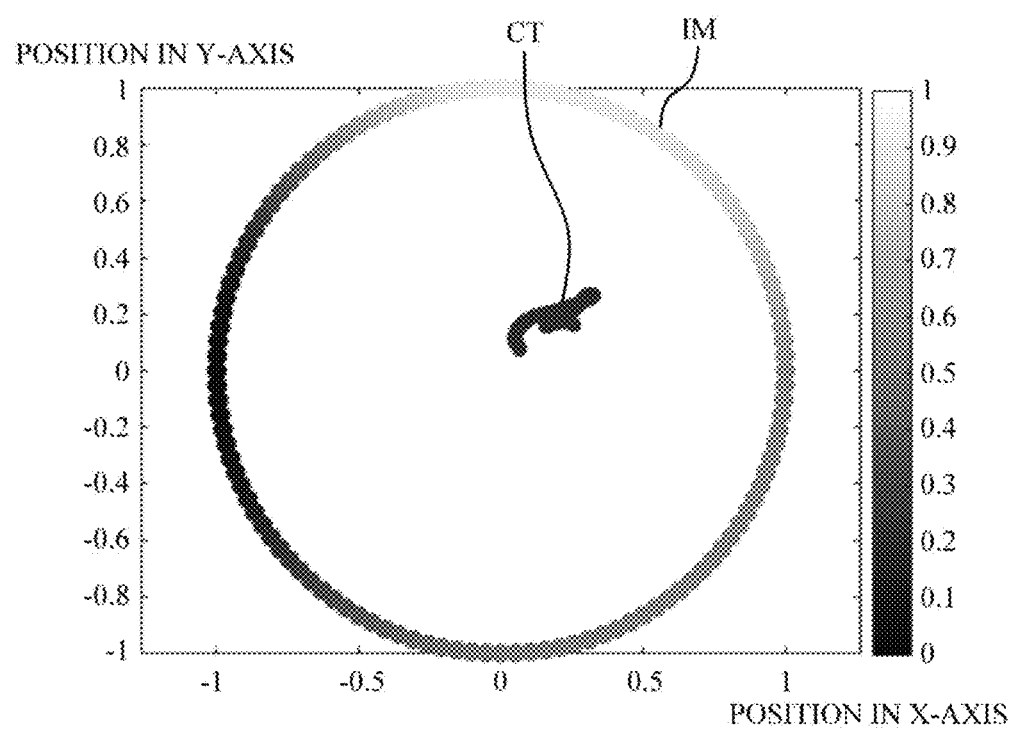
Figure 4F:
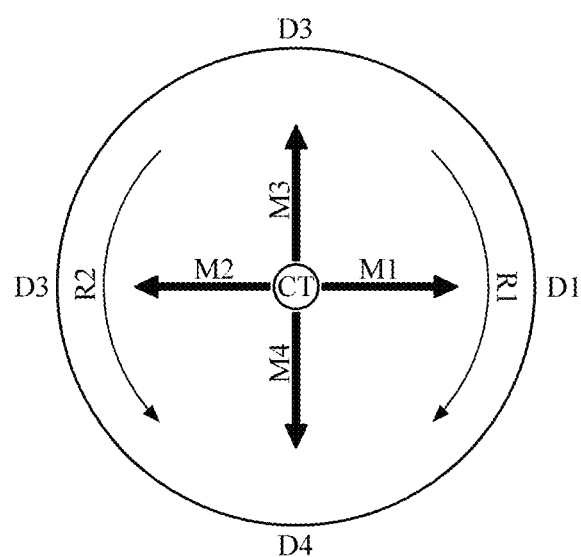

FIG. 4E is a diagram illustrating a trajectory CT that shows a change of a position of the center of gravity over a period of time. The processor 120 may track a change in position of the center of gravity and may detect a pattern of a change trajectory to control a function corresponding to the detected pattern by referring to the storage 230. FIG. 4F is a diagram illustrating predetermined patterns according to a change in position of the center of gravity, including patterns M1, M2, M3, and M4 in which the center of gravity moves linearly in a predetermined direction from a center CT, a pattern R1 in which the center of gravity moves in a curve from an upper position D3 to a right position D1 and then downward to a lower position D4, a pattern R2 in which the center of gravity moves in a curve from the upper position D3 to a left position D2 and then downward to the lower position D4, and the like. As described above, the processor 120 may control the function of moving in all directions and rotating in clockwise and counterclockwise directions. However, the patterns are not limited thereto, and even in the same pattern, the function control operation may be performed differently depending on devices or functions to be controlled.

FIGS. 5A to 5M are diagrams illustrating examples of performing function control. The function control illustrated in FIGS. 5A to 5M may be performed by a smartwatch 500, but the type of the device that performs the function control is not limited thereto.

Figure 5A:
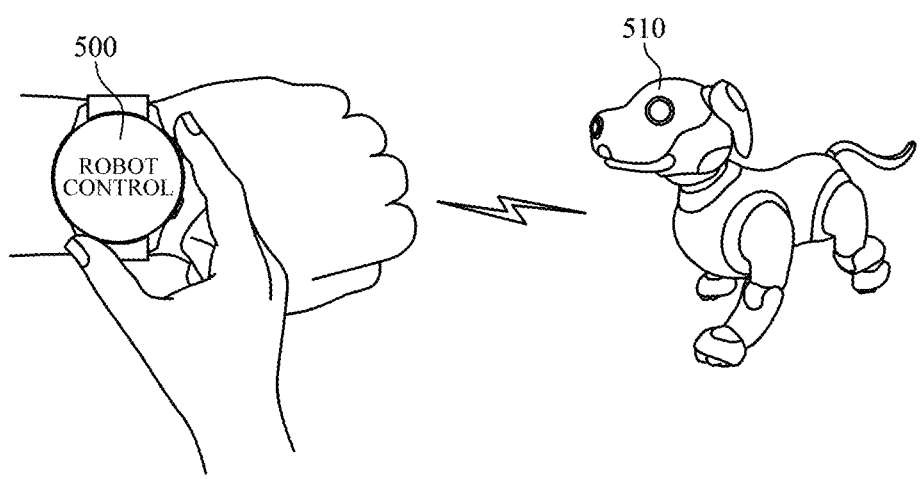
FIGS. 5A to 5M are diagrams explaining examples of performing function control.
Figure 5B:
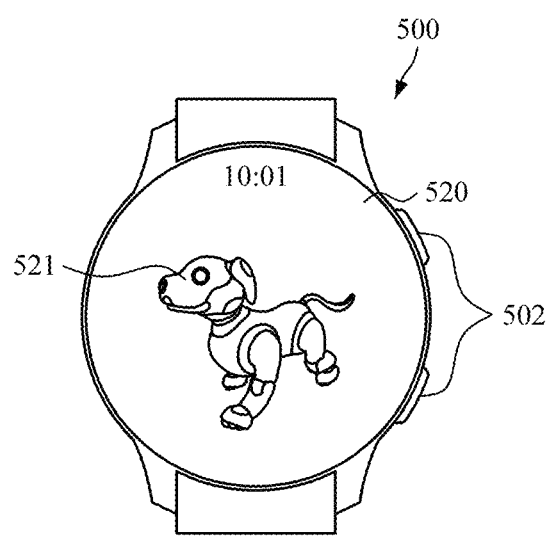
Figure 5C:
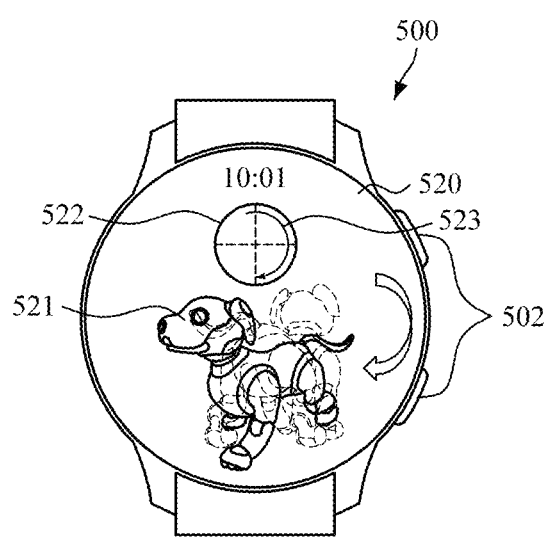

Referring to FIGS. 5A to 5D, a user may control a robot 510 while wearing the smartwatch 500 on the wrist. A user interface 520 for controlling the robot may be displayed on a display of the smartwatch 500, and a graphic object 521, such as a character or image of the controlled robot, may be displayed on the user interface 520 (FIG. 5B). In this case, a graphic object 523 representing a trajectory that shows a change of the center of gravity may be displayed in a predetermined area 522 of the display (FIG. 5C). When a user induces a change in the center of gravity by moving a main body of the smartwatch 500 worn on the wrist or pressing the main body to form a predetermined pattern (e.g., FIG. 4F), the processor 120 may control motion of the robot 510 (e.g., moving, enlarging/reducing, rotating, jumping, etc.) that corresponds to the pattern. In addition, when the user performs a selected gesture or action, the robot 510 may perform a corresponding motion (e.g., jumping, etc.). In this case, the selected action may include increasing pressure applied to the object while the center of gravity is located at a specific position, so that the intensity at the position of the center of gravity (intensity of a low-frequency band signal) may greater than or equal to a threshold value, or pressing or touching a side button 502 formed on the smartwatch 400, and the like. Along with the function control of the robot 510, the processor 120 may change the graphic object 521 in the user interface 520 in synchronization with the motion of the robot 510 (e.g., moving, enlarging/reducing, rotating, jumping, etc.).

Figure 5D:
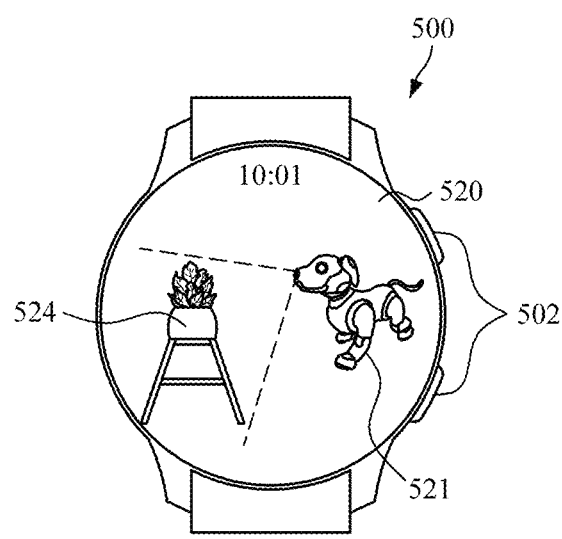
Figure 5E:
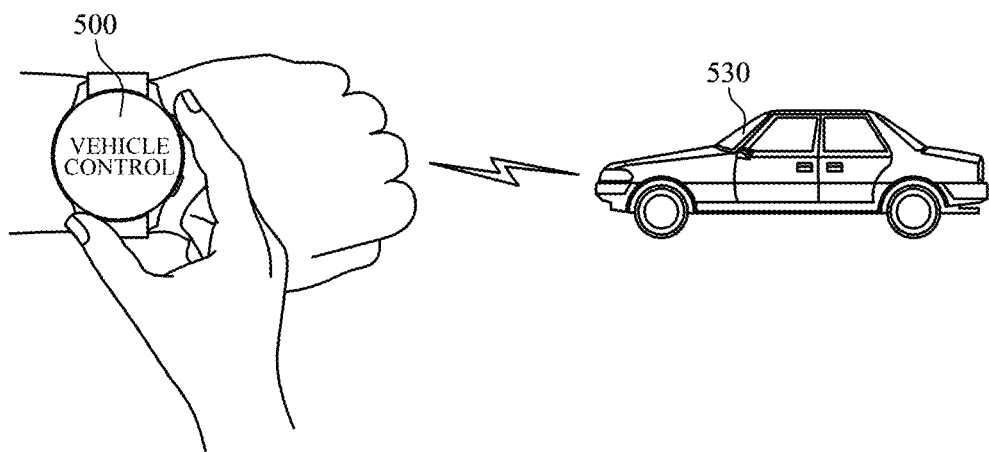

In addition, as illustrated in FIG. 5D, the processor 120 may receive data, e.g., an image 524 captured by a camera while the robot 510 moves, from the robot 510 and may display the received data on the user interface 520. If the aforementioned selected action is performed while the image is displayed, a currently displayed image may be stored in the storage.

Figure 5F:
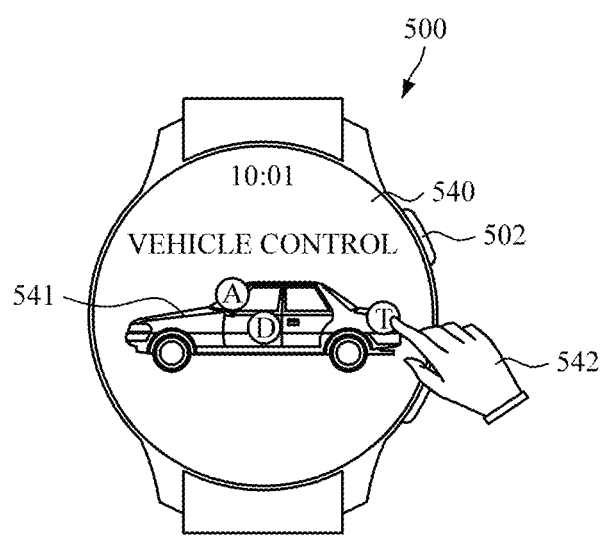
Figure 5G:
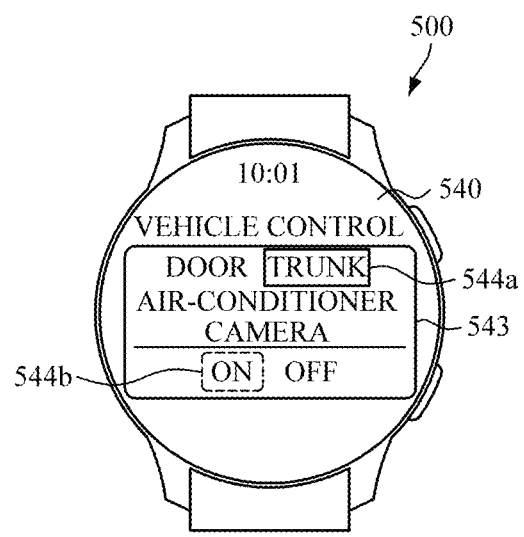

Referring to FIGS. 5E to 5H, the user may control a vehicle 530 by using the smartwatch 500. As illustrated in FIG. 5F, a user interface 540 for vehicle control may be displayed on the display of the smartwatch 500, and a graphic object 541, such as a character or image of the vehicle, may be displayed on the user interface 540. In addition, figures A, D, and T for guiding a control function (controlling air-conditioning, opening and closing the door, opening and closing the trunk, etc.) may be displayed on the graphic object 54. As illustrated in FIG. 5G, a menu 543 for controlling the vehicle may also be displayed. In addition, a graphic object 542, such as a shape of a hand that moves in synchronization with movement of the center of gravity, etc., or graphic objects 544a and 544b in the shape of colored windows and/or having an edge of a predetermined shape indicating that a specific item is selected from a menu, may be displayed so that the user may select the figures A, D, and T, or the menu 543 corresponding to a specific function to be controlled. As illustrated in FIG. 5C, a graphic object 523 indicating a change trajectory of the center of gravity may be displayed in the predetermined area 522 of the display.

Figure 5H:
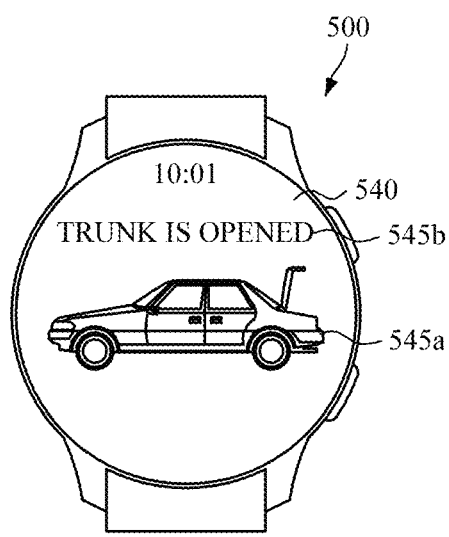

When a user performs the aforementioned selected action while moving the graphic object 542 to the figure D by changing the center of gravity (FIG. 5F) or moving the graphic objects 544a and 544b to trunk or ON in the menu (FIG. 5G), the trunk may be controlled to be opened, and a vehicle image 545a showing the opened trunk and/or a text message 545b, such as "the trunk is opened," may be output as illustrated in FIG. 5H.

Figure 5I:
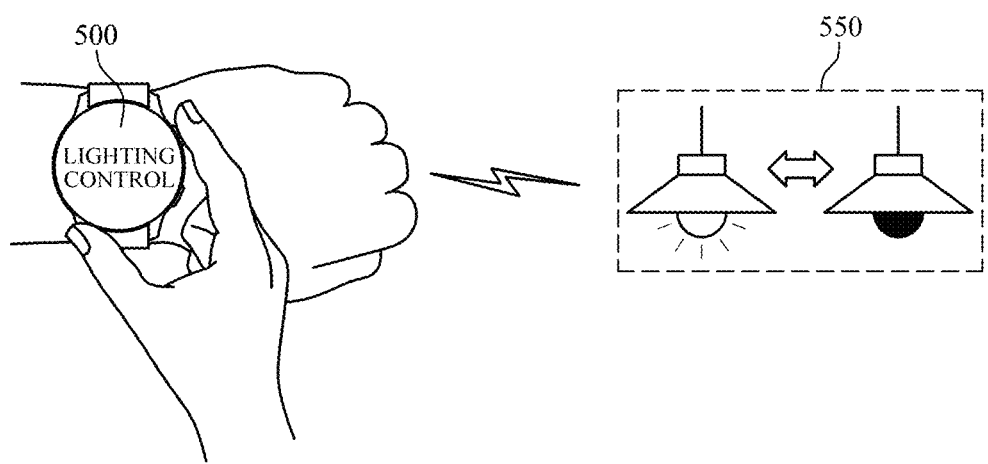
Figure 5J:
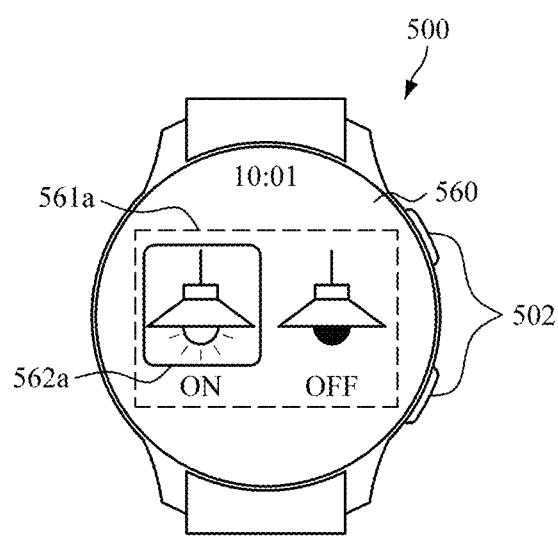
Figure 5K:
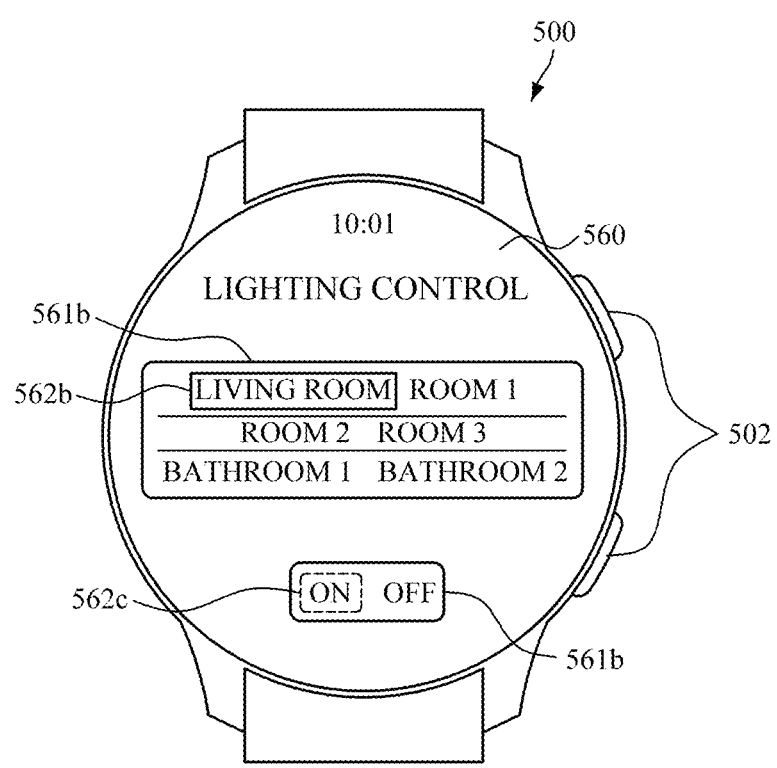

Referring to FIGS. 5I and 5K, a user may control a lighting device 550 by using the smartwatch 500. A user interface 560 may be displayed on the display of the smartwatch 500, and graphic objects, such as a lighting device image 561a and/or a menu 561b showing a position of the lighting device, may be displayed on the user interface 560. Further, graphic objects 562a, 562b, and 562c that move in synchronization with movement of the center of gravity may be displayed, and when a user performs the aforementioned selected action after moving the graphic objects 562a, 562b, and 562c to a specific menu by changing the center of gravity, an operation corresponding thereto may be performed.

While examples of controlling other devices 510, 530, and 550 are described above with reference to FIGS. 5A to 5K, the present disclosure is not limited to these examples. Other functions of the devices 510, 530, and 550, which are not described herein, may also be controlled, and a remote control function of TV or stereo system may also be performed. In addition, an operation of controlling machines in a smart factory, a controller function of Internet of Things (IOT) devices (home appliances, home network, etc.) may be performed.

Figure 5L:
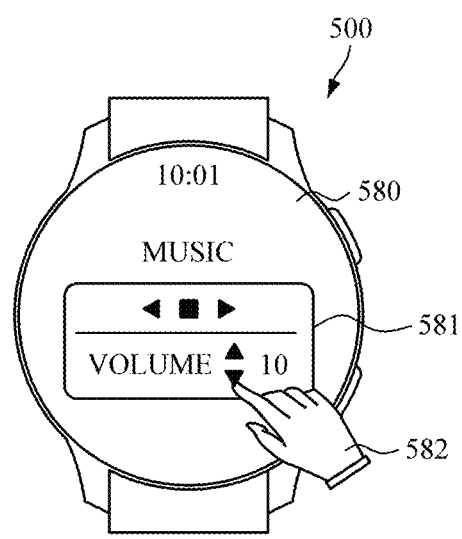
Figure 5M:
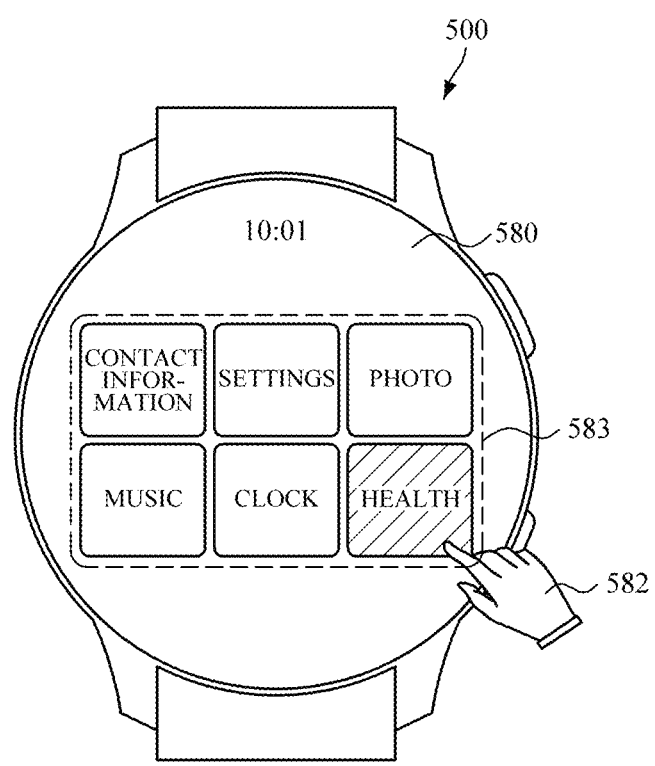

FIGS. 5L and 5M are diagrams illustrating examples of performing function control by the smartwatch 500. Referring to FIG. 5L, a user interface 580 for an application (e.g., music) currently running on the smartwatch 500 may be displayed, and a menu 581 for volume control of the application may be displayed. In addition, a graphic object 582 that moves according to a change in the center of gravity may be displayed, and after moving the graphic object 582 to a volume control button by moving the center of gravity, the user may control the volume by performing the aforementioned selected action. Referring to FIG. 5M, a widget 583 for controllable applications and a graphic object 582 may be displayed on the user interface 580, and when the user selects a specific widget (health) by moving the graphic object 582, an application corresponding thereto may be executed. The above examples are merely provided to allow for a clearer understanding of the present disclosure, and the present disclosure is not limited to these examples.

Figure 6:
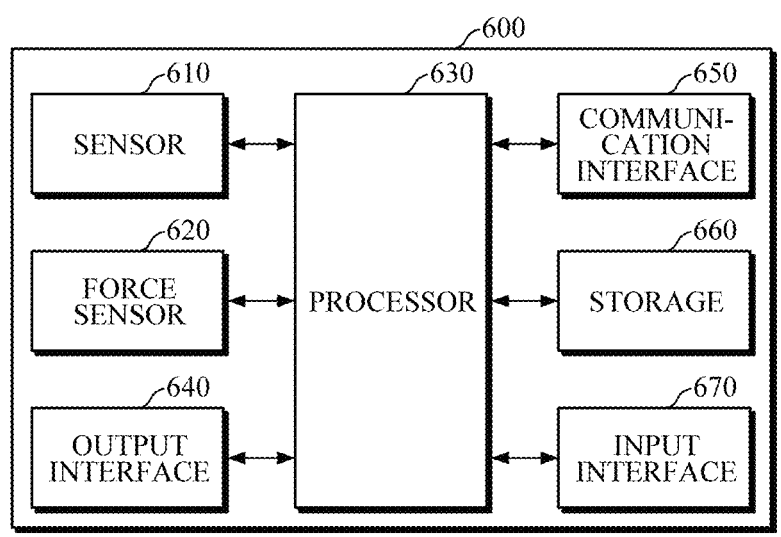
FIG. 6 is a block diagram illustrating an electronic device according to an embodiment of the present disclosure.
Figure 7:
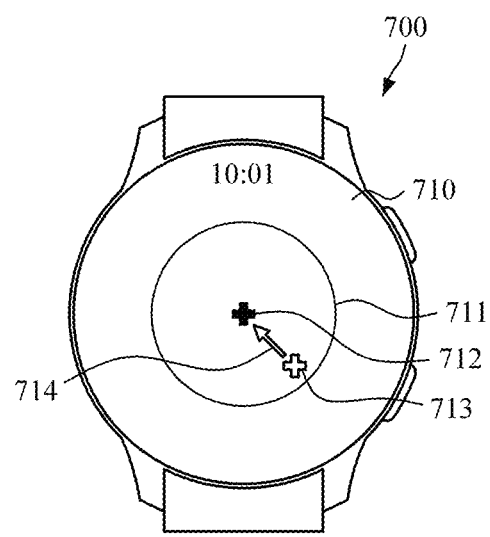
FIG. 7 is a diagram explaining an example of guiding a contact state.

FIG. 6 is a block diagram illustrating an electronic device according to an embodiment of the present disclosure. FIG. 7 is a diagram explaining an example of guiding a contact state.

Referring to FIG. 6, the electronic device 100 includes a sensor 610, a force sensor 620, a processor 630, an output interface 640, a communication interface 650, a storage 660, and an input interface 670. Some of the sensor 610, the force sensor 620, the output interface 640, the communication interface 650, the storage 660, and the input interface 670 may be omitted if necessary and may be mounted in another device which is physically separated. The following description will focus on functions or features not overlapping with those of the aforementioned electronic devices 100 and 200.

The force sensor 620 may measure force or pressure acting on the sensor 610 when a user places an object on the sensor 610 and gradually increases a pressing force thereon or when the user gradually decreases force after applying a force greater than or equal to a threshold value. The force sensor 620 may be disposed at an upper end or a lower end of the sensor 110. The force sensor 620 may include a strain gauge and the like, and may be formed as a single force sensor or a force sensor array. In this case, the force sensor 620 may be changed to a pressure sensor combined with the force sensor 620 and an area sensor or a pressure sensor in the form of an air bladder, and the like.

The processor 630 may selectively operate in a normal mode in which the electronic device 600 performs a normal function (clock, music, photo, etc.), in a function control mode in which the electronic device 600 generates a control command and performs the above control function, or in a bio-information estimation mode in which the electronic device 600 estimates bio-information. When a user selects the function control mode, the processor 630 may perform the above function control operation. The user may directly request bio-information estimation, or may request bio-information estimation in the function control mode as described above, and then enter the bio-information estimation mode.

In the bio-information estimation mode, the processor 630 may perform an operation of guiding a user to accurately place an object on a measurement area of the sensor 610 through the output interface 640. Referring to FIG. 7, the output interface 640 may display a circular measurement area 711 or a marker 712 indicating the center of the measurement area 711 on a display 710 of a smartwatch 700 under the control of the processor 630. When the user touches the sensor 610 with the object to measure a multi-channel PPG signal, the processor 630 may detect a center of gravity based on the multi-channel PPG signal. In response to the processor 630 detecting the center of gravity, the output interface 640 may display a marker 713 indicating a position of the detected center of gravity, as well as a marker 714 for inducing the user to move the center of the gravity to the center of the measurement area 711.

In addition, once the force sensor 620 measures a contact force acting between the object and the sensor 610, the processor 130 may receive the measured contact force to guide the user on a force to be applied by the user through the output interface 640.

When the multi-channel PPG signal and the contact force are measured by the sensor 610 and the force sensor 620 based on the guiding, the processor 630 may estimate bio-information based on the multi-channel PPG signal and the contact force. For example, the processor 630 may obtain an oscillometric waveform envelope that indicates a relationship between contact pressure and an amplitude of the PPG signal, and may estimate blood pressure by using the obtained oscillometric waveform envelope. The contact pressure may be a contact force value per se measured by the force sensor 120 or a value obtained by converting the contact force value into a pressure value by using a predefined conversion equation. Alternatively, in the case where an area sensor is provided, the processor 630 may convert the contact force value into a pressure value by using the contact force, measured by the force sensor 620, and a contact area measured by the area sensor.

The processor 630 may select some of the plurality of channels. For example, the processor 630 may select a predetermined number of channels in descending order from the highest intensity of low-frequency band signal values of the respective channels, and/or in order from the shortest distance between the respective channels and the center of gravity. Upon selecting a plurality of channels, the processor 630 may generate an oscillometric waveform envelope by integrating PPG signals of the selected channels to form a single PPG signal. The processor 630 may extract a feature value (a contact pressure value at a point of maximum amplitude, a contact pressure value corresponding to an amplitude value having a predetermined ratio to the maximum amplitude value, etc.) and may estimate blood pressure by inputting the extracted feature value to a blood pressure estimation model. The blood pressure estimation model may be defined as various linear or non-linear combination functions, such as addition, subtraction, division, multiplication, logarithmic value, regression equation, and the like, without specific limitation.

Figure 8:
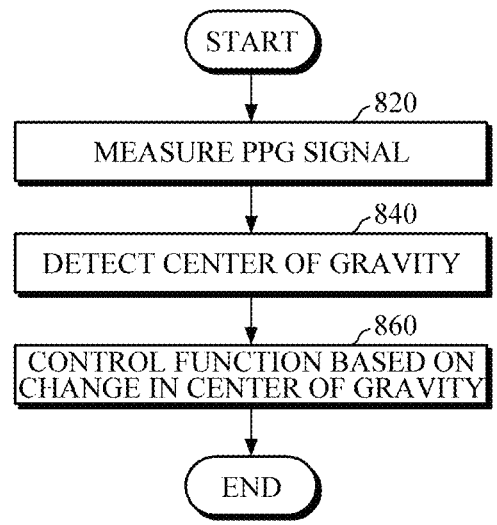
FIG. 8 is a flowchart illustrating a function control method according to an embodiment of the present disclosure.

FIG. 8 is a flowchart illustrating a function control method according to an embodiment of the present disclosure.

The method of FIG. 8 is an example of a function control method performed by the electronic devices 100 and 200 of FIG. 1 or FIG. 2, which are described in detail above, and thus will be briefly described below.

First, in response to a user's request for function control, the sensor may measure a multi-channel PPG signal from an object of the user in 820. In this case, multiple channels of the sensor may be arranged isotropically at a predetermined distance from the center of the sensor, and at least one of the light source and the detector may be disposed in the respective channels. For example, both the light source and the detector may be disposed in the respective channels. Alternatively, one of the light source and the detector may be disposed at the center of the sensor, and the other may be disposed in the respective channels.

Then, the electronic device may detect the center of gravity when the object presses the sensor in a measurement area of the sensor by using the multi-channel PPG signal in 840. The electronic device may extract low-frequency band signals by filtering PPG signals of the respective channels, may generate an intensity map by mapping the low-frequency band signal values of the respective channels to a measurement area, and may detect the center of gravity by using the generated intensity map. While touching the sensor with the object, the user may induce a change in the center of gravity by moving or pressing the main body or the object, and may input a gesture (moving or rotating another device, or a specific function thereof (camera, increasing or decreasing volume, changing channel, turning on/off lighting device, opening and closing vehicle door, etc.)) intended by the user.

Subsequently, the electronic device may control a function, desired by the user, based on the change in the center of gravity in 860. The user may request control of functions of another device, such as a robot, game console, TV, machine, Internet of Things (IOT) device, or functions of the electronic devices 100 and 200. The electronic device may identify a change pattern of the center of gravity detected in 840 and may control a function corresponding to the change pattern.

Figure 9:
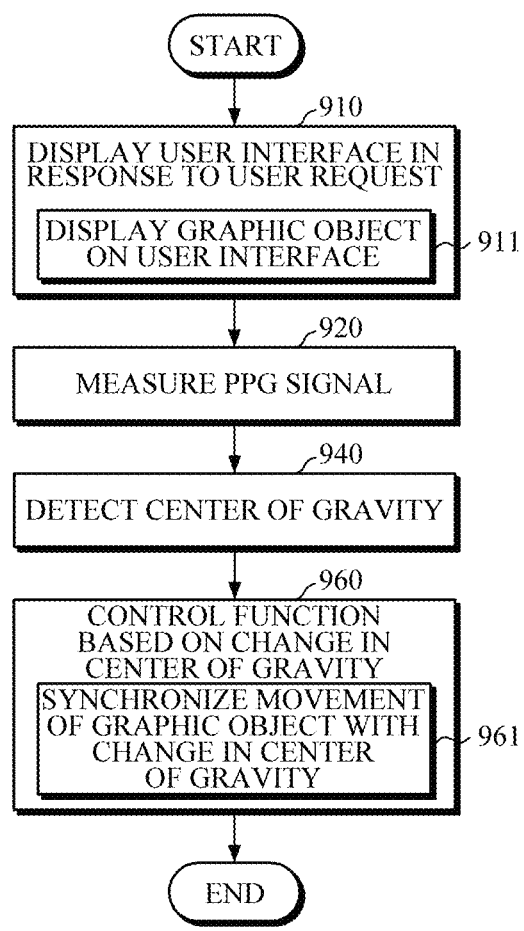
FIG. 9 is a flowchart illustrating a function control method according to another embodiment of the present disclosure.

FIG. 9 is a flowchart illustrating a function control method according to another embodiment of the present disclosure.

The method of FIG. 9 is an example of a function control method performed by the electronic devices 100 and 200 of FIG. 1 or FIG. 2, which are described in detail above, and thus will be briefly described below.

First, in response to a user's request for function control, the electronic device may display a user interface for function control on a display in operation 910. The user interface may be configured based on functions of a device to be controlled (e.g., the electronic devices 100 and 200 or another device such as robot, vehicle, lighting device, TV, Internet of Things (IOT) device, etc.), and functions thereof to be controlled, and the user interface may include graphic objects responsive to a change in center of gravity in operation 911.

Then, once the sensor measures a multi-channel PPG signal from an object of the user in operation 920, the electronic device may detect the center of gravity when the object presses the sensor in a measurement area of the sensor by using the multi-channel PPG signal in operation 940.

Subsequently, the electronic device may control a function, desired by the user, based on a change in the center of gravity in operation 960. The controlling of the function may include generating a control signal and transmitting the generated control signal to a device, as well as changing representation (movement, form, color, etc.) of a graphic object displayed on the user interface by synchronizing with the change in the center of gravity (operation 961) and/or a function control result.

Figure 10:
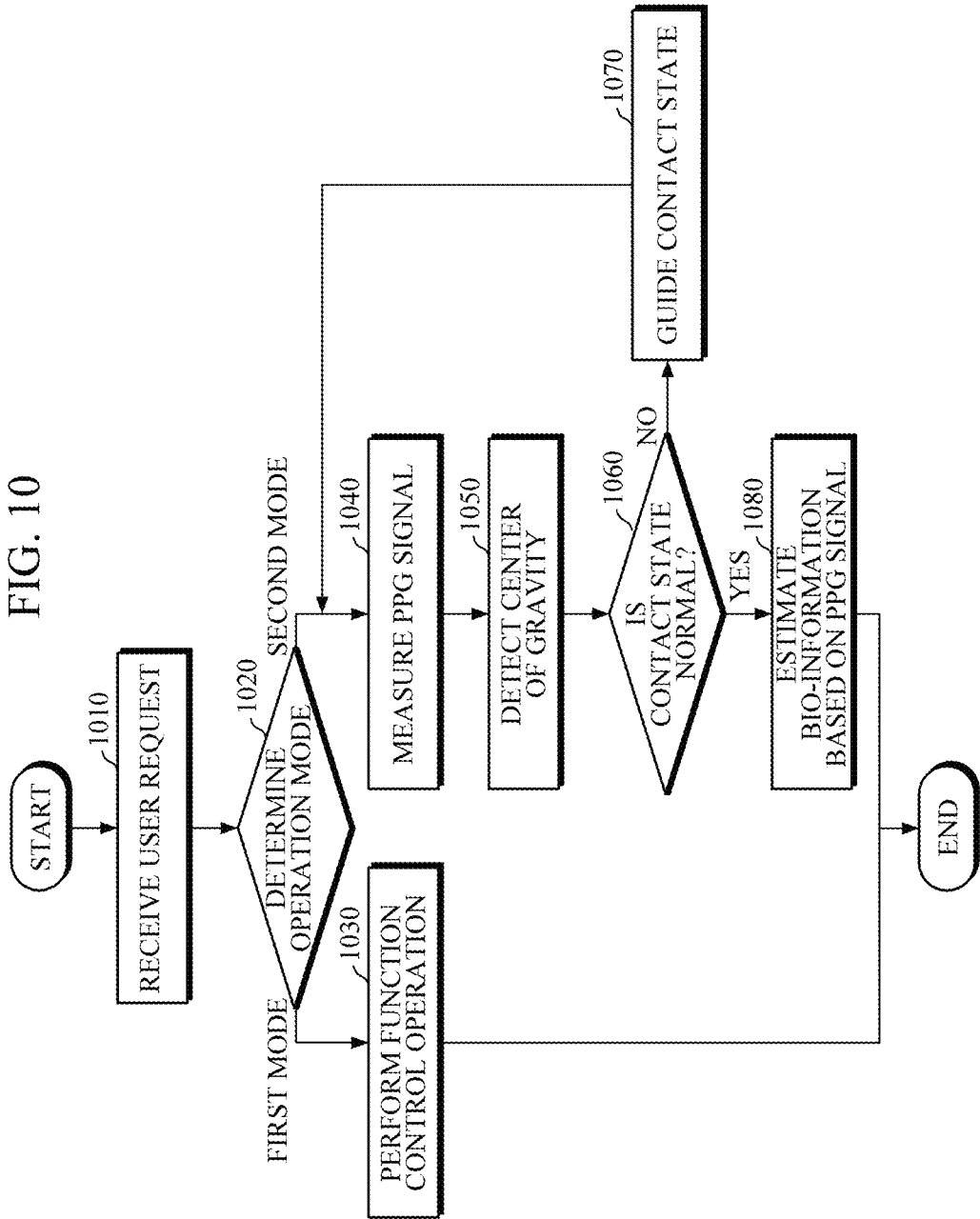
FIG. 10 is a flowchart illustrating a function control method according to yet another embodiment of the present disclosure.

FIG. 10 is a flowchart illustrating a function control method according to yet another embodiment of the present disclosure.

The method of FIG. 10 is an example of a function control method performed by the electronic device 600 of FIG. 6, which is described in detail above, and thus will be briefly described below.

First, upon receiving a user request in operation 1010, the electronic device may determine an operation mode in operation 1020. The operation mode may include a first mode for controlling a function and a second mode for estimating bio-information. If the operation mode is the first mode, the electronic device may perform a function control operation 1030 as described above. If the operation mode is the second mode, the electronic device may control the sensor to measure a PPG signal in operation 1040, and may detect a center of gravity based on the measured multi-channel PPG signal in operation 1050. The electronic device may determine a contact state, such as contact position, pressure, etc., based on the detected center of gravity in operation 1060. If the contact state is not normal, the electronic device may guide a contact state based on the detected center of gravity in operation 1070, and if the contact state is normal, the electronic device may estimate bio-information by using the measured multi-channel PPG signal in operation 1080.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An electronic device comprising:
a photoplethysmography (PPG) sensor having a plurality of channels arranged isotropically, and comprising a first light source located at a center of a measurement area of the PPG sensor and a plurality of first detectors located at a boundary of the measurement area, or a second detector located at the center of the measurement area and a plurality of second light sources located at the boundary of the measurement area; and
a processor configured to:
detect a center of gravity of an external force applied to the measurement area of the PPG sensor by an object, based on PPG signals that are detected from the plurality of channels when the object is in contact with the measurement area of the PPG sensor; and
generate a control command based on a change in the detected center of gravity, wherein the processor is further configured to:
detect a shift in the center of gravity of the external force applied to the measurement area of the PPG sensor when the object changes a direction of the external force while maintaining a same contact position with respect to the measurement area of the PPG sensor.

2. The electronic device of claim 1, wherein the processor is further configured to:
identify a pattern in a trajectory of the center of gravity of the external force by monitoring the change in the detected center of gravity of the external force over time; and
determine the control command corresponding to the pattern in the trajectory of the center of gravity of the external force from a storage of the electronic device.

3. The electronic device of claim 1, wherein the processor is further configured to:

obtain low-frequency band signal values of the PPG signals that are detected from the plurality of channels, in a predetermined low frequency band; and detect the center of gravity based on the low-frequency band signal values of the plurality of channels.

4. The electronic device of claim 3, wherein the processor is further configured to:

generate an intensity map by mapping the obtained low-frequency band signal values of the plurality channels to a circular circumference; and detect the center of gravity based on the intensity map.

5. The electronic device of claim 4, wherein the processor is further configured to:

obtain low-frequency band signal values for a plurality of virtual channels arranged on the circular circumference by performing interpolation on the low-frequency band signal values of the plurality of channels that are arranged on the circular circumference; and generate the intensity map based on the low-frequency band signal values of the respective channels and the low-frequency band signal values of the virtual channels to the circular circumference.

6. The electronic device of claim 1, further comprising a main body comprising the PPG sensor and the processor are disposed, wherein the processor is further configured to detect the change in the detected center of gravity that is caused by at least one of a change in pressure applied to the PPG sensor or the main body, and movement of the main body or the object, while the PPG sensor is in contact with the object.

7. The electronic device of claim 1, further comprising a main body comprising the PPG sensor, the processor, and an input interface, wherein the processor is further configured to generate the control command based on the change in the detected center of gravity.

8. The electronic device of claim 1, wherein the processor is further configured to control the electronic device or an external device connected to the electronic device, via the control command.

9. The electronic device of claim 8, wherein the processor is further configured to generate the control command to control a function of estimating bio-information, based on the PPG signals of the plurality of channels.

10. The electronic device of claim 8, further comprising a communication interface configured to transmit the control command to the external device.

11. The electronic device of claim 1, further comprising a display, wherein in response to a user's request for control, the processor is further configured to provide a user interface for controlling the display via the control command.

12. The electronic device of claim 11, wherein the processor is further configured to control the user interface to display a graphic object responsive to the change in the center of gravity on the display, and change representation of the graphic object in synchronization with the change in the detected center of gravity.

13. The electronic device of claim 11, further comprising a communication interface configured to receive data from another electronic device, wherein the processor is further configured to display a graphic object associated with the received data on the user interface.

14. A control method using an electronic device, the control method comprising:

by a photoplethysmography (PPG) sensor having a plurality of channels arranged isotropically, measuring PPG signals from an object through the plurality of channels, wherein the PPG sensor comprises a first light source located at a center of a measurement area of the PPG sensor and a plurality of first detectors located at a boundary of the measurement area, or a second detector located at the center of the measurement area and a plurality of second light sources located at the boundary of the measurement area;

detecting a center of gravity of an external force applied to the measurement area of the PPG sensor by the object, based on the PPG signals that are detected from the plurality of channels when the object is in contact with the measurement area of the PPG sensor; and generating a control command based on a change in the detected center of gravity; and detecting a shift in the center of gravity of the external force applied to the measurement area of the PPG sensor when the object changes a direction of the external force while maintaining a same contact position with respect to the measurement area of the PPG sensor.

15. The control method of claim 14, wherein the detecting of the center of gravity comprises:

obtaining low-frequency band signal values from the PPG signals that are detected from the plurality of channels, in a predetermined low frequency band; and detecting the center of gravity based on the low-frequency band signal values of the plurality of channels.

16. The control method of claim 15, wherein the detecting of the center of gravity comprises:

generating an intensity map by mapping the low-frequency band signal values of the plurality of channels to a circular circumference; and detecting the center of gravity based on the intensity map.

17. The control method of claim 14, further comprising, in response to a user's request for control, displaying a user interface for controlling a display of the electronic device according to the control command.

18. The control method of claim 17, wherein the displaying of the user interface comprises:

displaying a graphic object responsive to the change in the center of gravity on the user interface; and changing representation of the graphic object in synchronization with the change in the detected center of gravity.

19. An electronic device comprising:

a memory including one or more instructions; and one or more processors which, in response to a user's request, are configured to execute the one or more instructions to selectively perform a function control operation and a bio-information estimation operation, wherein the function control operation comprises:

receiving, from a photoplethysmography (PPG) sensor having a plurality of channels arranged isotropically, PPG signals, wherein the PPG sensor comprises a first light source located at a center of a measurement area of the PPG sensor and a plurality of first detectors located at a boundary of the measurement area, or a second detector located at the center of the measurement area and a plurality of second light sources located at the boundary of the measurement area;

detecting a center of gravity of an external force applied to the measurement area of the PPG sensor by an object, based on the PPG signals that are detected from the plurality of channels when the object is in contact with the measurement area of the PPG sensor;

performing the function control operation based on the detected center of gravity; and detecting a shift in the center of gravity of the external force applied to the measurement area of the PPG sensor when the object changes a direction of the external force while maintaining a same contact position with respect to the measurement area of the PPG sensor.

* * * * *